(12) United States Patent
Jacob et al.

(10) Patent No.: US 7,042,577 B1
(45) Date of Patent: May 9, 2006

(54) ARCHITECTURES FOR HIGH-RESOLUTION PHOTOMASK PHASE METROLOGY

(75) Inventors: James Jeffery Jacob, Watsonville, CA (US); Andrew John Merriam, San Francisco, CA (US)

(73) Assignee: ACTINIX, Scotts Valley, CA (US)

( * ) Notice: Subject to any disclaimer, the term of this patent is extended or adjusted under 35 U.S.C. 154(b) by 416 days.

(21) Appl. No.: 10/619,525

(22) Filed: Jul. 15, 2003

Related U.S. Application Data

(60) Provisional application No. 60/396,220, filed on Jul. 16, 2002.

(51) Int. Cl.
   G01B 9/02 (2006.01)
   G01N 21/00 (2006.01)

(52) U.S. Cl. .................. 356/511; 356/239.3; 356/237.4

(58) Field of Classification Search ................ 356/489, 356/495, 511, 515, 521, 237.3, 237.4, 239.3
See application file for complete search history.

(56) References Cited

U.S. PATENT DOCUMENTS

| | | | |
|---|---|---|---|
| 5,710,631 A * | 1/1998 | Bou-Ghannam et al. .... | 356/495 |
| 6,445,453 B1 * | 9/2002 | Hill ............................. | 356/450 |
| 6,559,953 B1 * | 5/2003 | Davids ........................ | 356/521 |
| 2002/0148955 A1 * | 10/2002 | Hill ............................. | 250/234 |

OTHER PUBLICATIONS

Kusunose et al. "Direct Phase-Shift Measurement with Transmitted Deep-UV Illumination", in Proceedings of the SPIE vol. 2793 pp. 251-260 (1996).

* cited by examiner

Primary Examiner—Gregory J. Toatley, Jr.
Assistant Examiner—Patrick Connolly

(57) ABSTRACT

We disclose several instrument architectures for the measurement of arbitrary phase retardation on advanced lithography photomasks. These architectures combine traditional interferometric techniques with high-magnification UV microscopy. Features are interrogated using a multitude of phase probes, formed by a imaging a number of variable apertures back-illuminated by phase-coherent beams, onto the surface of the photomask with a given demagnification. The size, spacing, and orientation of the phase probes may be adjusted to suit photomask feature geometries. Means are provided to vary the relative optical phase between the phase probes. These phase probes both reflect from and transmit through the photomask; the stationary, non-localized interference fringes, formed in the regions of phase probe electric field overlap, contain information on the optical path difference between the two probes. The spatial resolution of these measurements is limited only by the resolution limit of the UV microscope, which may significantly exceed the capability of existing tools.

20 Claims, 4 Drawing Sheets

ARCHITECTURES FOR HIGH-RESOLUTION PHOTOMASK PHASE METROLOGY

CROSS-REFERENCE TO RELATED APPLICATION

This application claims the benefit of U.S. Provisional Patent Application Ser. No. 60/396,220, "Architectures for high-resolution photomask phase metrology" by J. J. Jacob and A. J. Merriam, filed Jul. 16, 2002, which is incorporated herein by reference.

BACKGROUND OF THE INVENTION

The manufacture of integrated circuit devices involves the processing of a semicondutor wafer through sequential layers to add or remove material. Optical projection lithography, or photolithography, is the most common process used around the world to pattern each layer onto the wafer. The wafer is covered with a material that is sensitive to light called a photoresist. The photoresist is then selectively exposed using a patterned photomask in an exposure tool: a stepper, a scanner, or a contact printer. The developed photoresist is the positive or negative image of the photomask, and acts as a physical stencil for transferring a pattern on the photomask to the wafer through the process of etching. State-of-the-art photolithography has enabled the semiconductor industry to produce sub-wavelength features and to keep pace with "Moore's law". This capability is due in large part to the recent introduction of advanced phase-shift photomasks (PSM) and optical proximity correction (OPC) technology. The increase in complexity of these photomasks has been reflected by large increases in PSM costs, and has made repair of defective photomasks an attractive alternative to replacement.

Inspection of masks using phase-shifting and OPC technologies is a difficult task, but necessary to ensure the initial and subsequent fidelity of the photomasks throughout the manufacturing process. Patterns on the photomasks must meet stringent criteria for size, shape, spacing, orientation, overlap, and placement of features. Defects must be repaired to prevent replication of errors across the printed wafers. There are two basic types of PSMs: embedded-attenuator PSMs (EAPSM), and alternating-aperture PSMs (AAPSMs) or "Levenson masks". EAPSMs deposit a layer of partially-opaque such as molybdenum silicide (MoSi) or some other compound to effect phase shifts; the transmission of a layer with thickness sufficient for a half-wave of phase shift displays approximately 5–10% transmission. AAPSM or Levenson masks remove controlled amounts of quartz photomask substrate to effect the phase changes, without depositing attenuating layers. In either case, features are designed to cause a variety of phase shifts (0 degrees, 60, 90, 180, etc.) in order to produce a given aerial image pattern. If the construction of the photomask is incorrect, so that, for example, a phase shift of a designed 180 degree shift feature is instead, say, 170 degrees, the desired feature may not print on the wafer, possibly leading to device failure. This is a typical photomask phase defect which must be identified and corrected before wafer production can continue.

What is needed is a tool for inspecting advanced photomasks to determine errors in phase and amplitude with high spatial resolution and accuracy. Currently, photomasks are usually inspected with a scanning optical microscope. However, phase information is lost since it is the light intensity, rather than the electric field amplitude, that is integrated at each location on a mask. Generally, interferometric techniques, which provide information about the phase of the optical beams, are required in order to obtain information on optical path difference (OPD).

One example of interferometric techniques applied to phasemask metrology may be found in U.S. Pat. No. 6,559,953. In '953, two phase-coherent beams with a controllable phase difference are combined on a CCD detector. One beam is first passed through a region on the photomask defined by a variable pupil, while the other beam serves as a uniform reference. The fringe pattern thus generated, in conjunction with several other 'control' interferograms, is used to determine the transmission and phase of the photomask region. No imaging components are employed in the setup (unity magnification), which emphasizes the need for collimated light beams. From a photomask metrology perspective, the primary drawback of '953 is that the spatial resolution of the phase and transmission measurements is limited by the pixel size of the CCD detector, which is on the order of several micrometers. This limitation precludes the use of '953 to perform metrology where it is most needed: on the sub-micron features found on advanced photomasks.

A second example, combining interferometric techniques with microscopy to perform phase metrology, is described in H. Kusunose et al., "Direct phase-shift measurement with transmitted deep-UV illumination", Proceedings of the SPIE Vol. 2793 pg. 251–260 (1996). Kusunose uses a lateral-shearing interferometer to combine two phase-coherent images, each of which has passed through the photomask slightly displaced from the other. The measurement is obtained by a photosensitive detector, mounted behind a final turning mirror, in the center of which a small hole has been drilled. The technique relies upon the quality of the microscope images, and thus the measurement precision and repeatability depends on the aberrations and NA of the optics within the microscope.

SUMMARY OF THE INVENTION

The present invention combines traditional interferometric techniques with high-magnification UV microscopy. The use of high-magnification imaging circumvents the resolution limitations of the prior art. The principles of the phase measurement techniques described in this patent are loosely based upon Young's $19^{th}$-century two-slit interference experiment. In Young's experiment, a spatially coherent wavefront is incident upon a screen containing two slits. In this description, spatial coherence refers to the existence of a fixed optical phase relationship between different arbitrary points chosen on a plane oriented perpendicularly to the direction of propagation. A beam is said to be spatially coherent when different points on this plane (which can be chosen at any position along the beam's travel) which are separated by at least half of one beam-width display a fixed phase relationship. The output of many lasers displays a large degree of spatial coherence. Young's wavefront, derived from an incoherent incandescent or 'thermal' source, is made spatially coherent by first passing the light through a small pinhole aperture. The spatially-coherent wavefront is divided in two parts as it passes through the slits, and then propagates to a photographic plate mounted some distance beyond the screen. When the plate is developed, a pattern of fine fringes of light and darkness may be observed, the spacing of which depends upon the separation of the slits and the wavelength of light used. The fringe pattern results from the interference of the two wavefronts, which may be constructive (resulting in a bright fringe) or destructive (dark fringe), depending upon the optical path difference (OPD) of these wavefronts. This OPD is different for each position on the plate; lines of constant light or darkness correspond to lines where the OPD between the two wavefronts is a constant. If a partially opaque plate with some unknown optical thickness is placed in front of one of the slits, the fringe pattern on the photographic plate may be observed to shift. This shift is due to a phase bias introduced by the unknown plate, and may be used to determine the optical thickness of said plate.

In the present phase measurement architectures, a high-spatial coherence light source such as a laser is employed, that ideally operates at the wavelength(s) at which the photomasks are employed (the so-called actinic wavelength): 248 nm for the KrF lithography generation, 193.4 nm for ArF lithography, and 157.63 nm for F2 lithography. A portion of this light is utilized for imaging purposes in a standard UV microscope, while the remainder is diverted to an interferometric/beam processing module. This module, the construction of which will be discussed later, breaks the incident beam into two or more phase-coherent beams and passes this light through a multitude of apertures. The light from these back-illuminated apertures is coupled into the UV microscope and imaged with a large demagnification factor onto the surface of the test photomask. In practice, an advanced, high-numerical-aperture (NA) objective lens is used with sub-200 nm illumination wavelengths, so that the system's optical magnification is between 100 and 200 and Rayleigh resolution between 0.150 microns and 0.20 microns. As an example, using 20-micron pinhole apertures in the interferometric module, and a system magnification/de-magnification of 100, the size of the imaged apertures on the mask, which determines the position and spatial resolution of the measurement, is 0.2 microns. The de-magnified apertures are separated by some adjustable amount on the photomask, and form the "slits" a la Young's experiment, but are referred to as "phase probes" in this Application. The aperture plane in the interferometric module is positioned par-focally with the main microscope imaging camera (typically a UV-sensitive CCD camera), so that both the phase probes and the photomask surface are simultaneously in focus. Typically, one probe is passed through the mask substrate, and the other through the feature of interest with an unknown phase profile. The size, spacing, and orientation of the phase probes may be adjusted to suit photomask feature geometries by independently moving the back-illuminated apertures. In transiting different points on the photomask, the optical waves emanating from the probes may accrue a certain relative phase difference. Due to the spatially-coherent light source and the interferometric module, the probes are phase coherent, and the interference of these beams gives rise to a set of high-contrast, stationary, non-localized fringe patterns below and above the photomask. Whether the fringes are collected above or below the photomask (reference FIGS. 1 and 2) depends on the type of photomask. EAPSMs are best measured in transmission, so that the fringes are measured beneath the photomask, while AAPSMs are ideally suited to reflection-mode measurements, wherein the fringes are measured above the photomask. The structure and position of these fringes depends upon the phase shift between the two phase probes, and this structure is used to determine the relative phase shift of the photomask feature. The majority of the extended interferometer is common-path, so that the fringe patterns are quite stable over time without active environmental controls.

In these types of interferometric measurement, there are always unknown static phase shifts associated with the interferometric path length, and the various components involved with the imaging. The static phase, which is also sensitive to environmental conditions, combines with the unknown phase shift of the queried photomask feature, and cannot in general be determined from ab initio calculations, but can be removed by taking the difference between two separate phase shift measurements since it is the same for each measurement. Hence, for each measurement of photomask feature phase shift, two phase shift measurements are generally required: one with both probes imaged onto the mask substrate, and one with one of the probes imaged onto the photomask feature of interest. If these two measurements are performed in a timely manner, the static phase shift will not change, and will be cancelled identically. When an actinic light source is employed, the OPD of the unknown photomask feature is exactly equal to the degree of fringe shift between the two measurements, and no additional dispersion calculations or assumptions are necessary.

The fact that photomask OPD information is not deduced from an image per se, but rather from a two-point measurement of actinic fringe shift, offers three distinct advantages of this architecture compared to the prior art. First, the fringe detection can occur anywhere within the fringe field. Second, the measurement precision, accuracy, and repeatability are not constrained by the aberrations of the microscope optics. Third, there is no dependence of measurement accuracy upon the numerical aperture of the microscope.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE INVENTION

Figure 1:
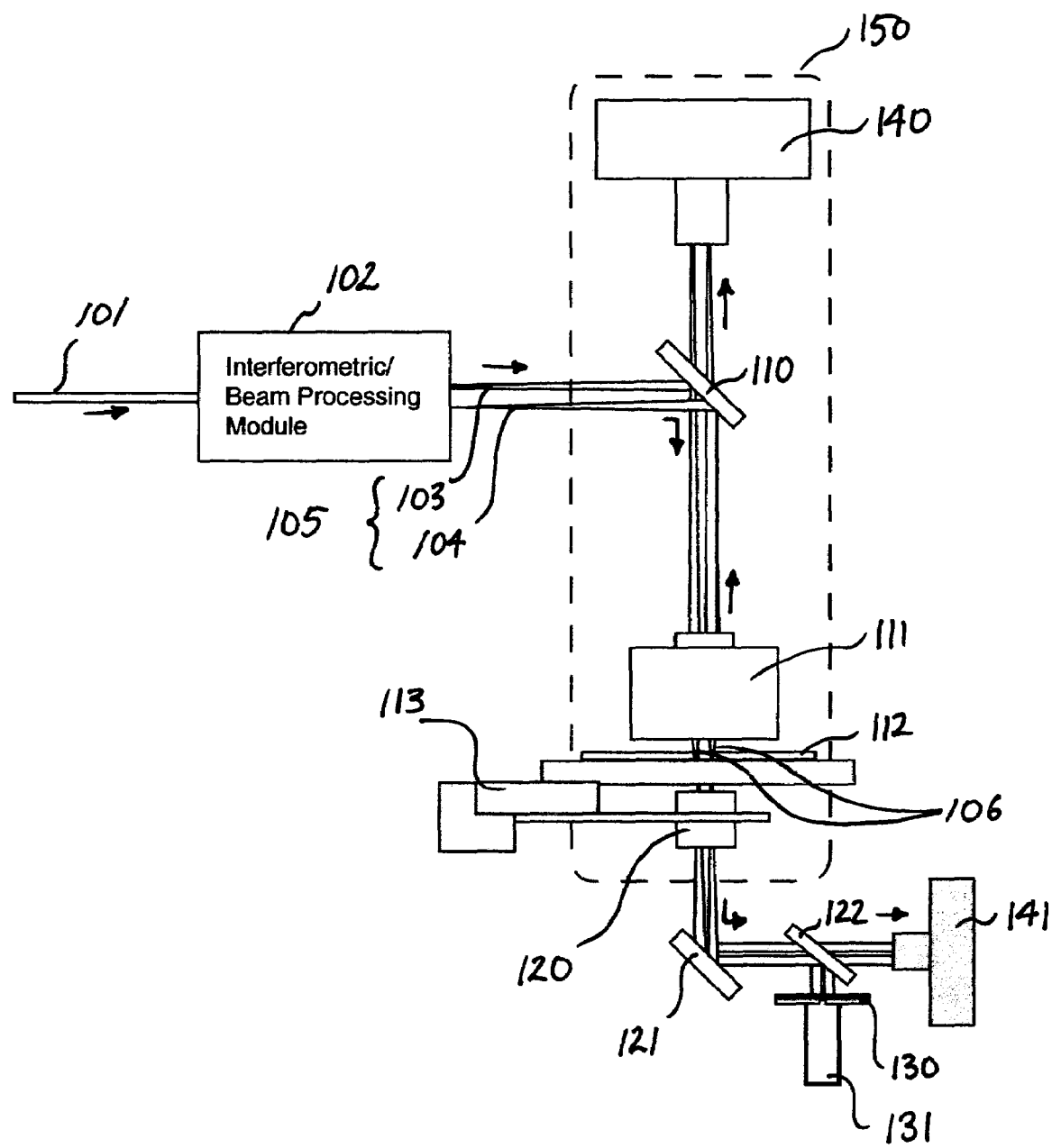
FIG. 1 A schematic diagram of a first embodiment of a phase measurement architecture using transmitted fringes according to the present invention.

FIG. 1 shows the overall layout of a preferred embodiment of an architecture for phase measurement using transmitted fringes. The light 101 from a spatially-coherent light source enters an interferometric beam processing module 102. In the preferred embodiment, this module, which will be described in greater detail presently, splits the incident light 101 into two phase-coherent components 103 and 104 with identical optical polarization. (Note that the portion of the optical apparatus usually devoted to transillumination of the photomask has been removed for clarity, as it is not required for the phase measurement process.) The phase-coherent components 105 are introduced into a transmission optical microscope 150 using beam-combiner 110. Note that in FIG. 1, as well as in subsequent figures, the small arrows next to beam components 101, 205, etc., indicate the direction of electromagnetic propagation. Phase-coherent components 105 are reflected down through a high-numerical-aperture (NA) objective lens 111. The objective lens 111 images the back-illuminated apertures (e.g., 340 or 540, depending upon the specific embodiment of the module) in module 102 with de-magnification near the surface of photomask 112 under study, to form the 'phase probes' 106. Light from phase probes 106 is both transmitted through photomask 112 downwards, and reflected upwards from it Both transmitted and reflected light may contain phase information. That portion of light reflected from the photomask is collected by objective lens 111 and propagates upwards, retracing the original path. Once this reflected fringe light reaches beamsplitter 110, a portion (typically 50%) passes through to a UV-sensitive camera 140. Camera 140 and the apertures in module 102 are positioned equidistantly (par-focally) from beamsplitter 110, so that the image of the phase probes appears focussed concurrently with the normal microscope image of the transilluminated photomask. In this fashion, the tool operator can determine the extent and position of the phase probes relative to features of interest on photomask 112. Photomask 112 is mounted on a stage 113 that allows the photomask position to be varied relative to the optic axis of the microscope.

That portion of phase probes 106 transmitted through photomask 112 is collected by a condenser lens 120. The light from the phase probes diverges rapidly below photomask 112, and because the probes are phase-coherent, a series of stationary, non-localized interference fringes occur in the overlapped portions of the transmitted light. The combined light reflects from partial reflector 121 (illumination light for microscope images, not shown, is generally coupled into the microscope through reflector 121) and is partially reflected by a second beamsplitter 122 onto a photodetector package consisting of a small aperture 130 located in front of a photo-sensitive detector (e.g., a PMT or Si photodiode) 131. Because fringe detector 131 is maintained at a fixed position during the measurements, the imaging performance of the microscope components does not degrade measurement accuracy or repeatability. If desired, beamsplitter 122 may be installed to allow transmitted fringe light to expose a second VUV-sensitive camera 141. In this fashion, the entire fringe pattern may be captured simultaneously (although now with effects from microscope aberrations).

Figure 2:
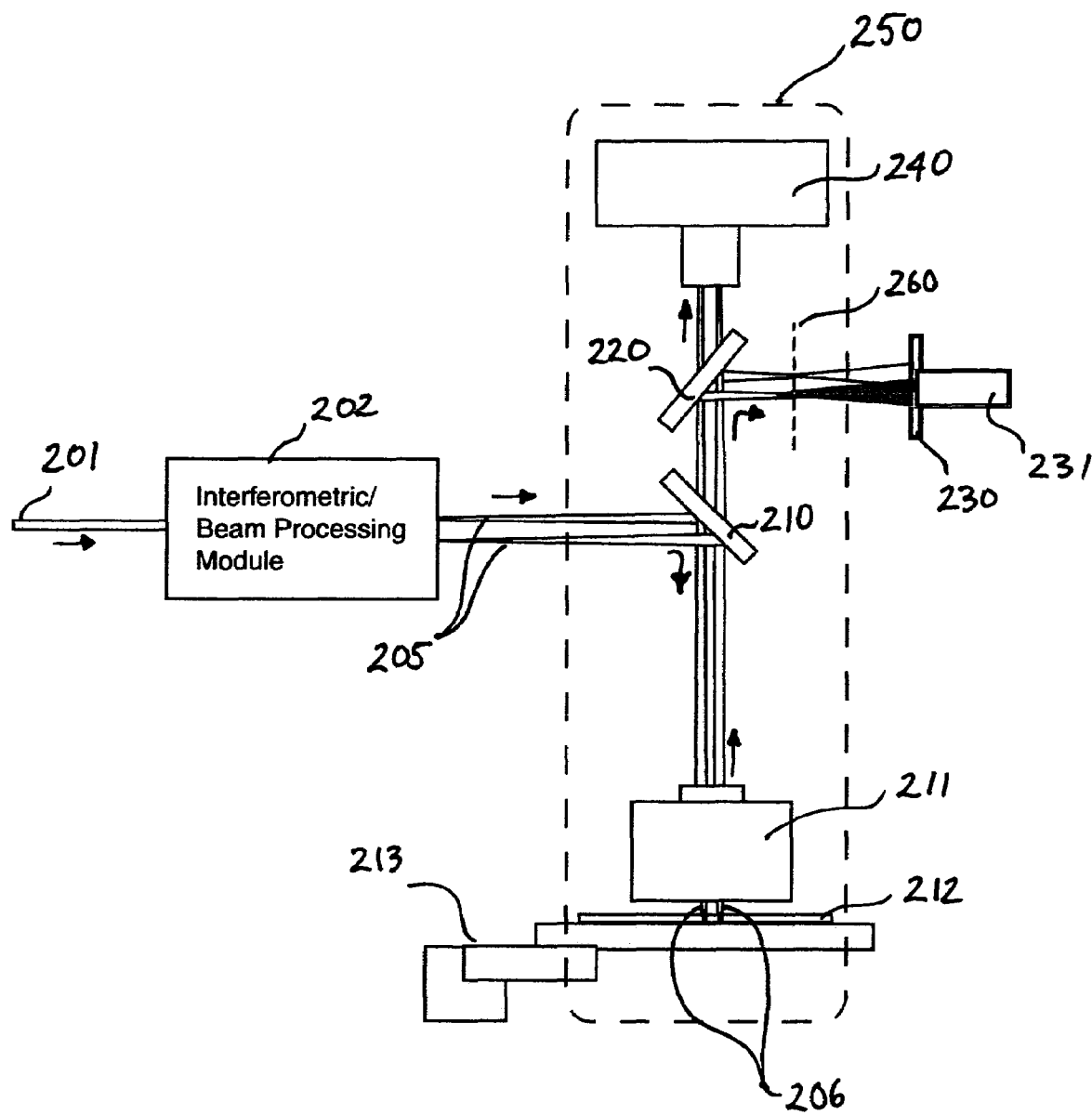
FIG. 2 A schematic diagram of a second embodiment of a phase measurement architecture using reflected fringes according to the present invention.

In addition to transiting the photomask, a portion of the phase probes' wavefronts reflect from the surface of the photomask and are imaged to the same camera system used for the high-resolution photomask imaging. This allows for a second, reflection mode of phase measurement: fringe structure is generated in the region of coherent probe wavefront overlap and may be detected (as in the transmissive case) either by a camera or non-imaging photodetector. A preferred embodiment of a reflection-mode architecture is shown in FIG. 2. Reflection mode detection is ideally suited for AAPSMs, and for EUV lithography-generation reflective photomasks. In the reflection-mode architecture, coherent beam components 205 created by module 202 are introduced to a reflection-mode optical microscope 250, wherein objective lens 211 functions as both objective and condenser. The main imaging camera 240 has been initially aligned with the other microscope components to provide a sharp image of photomask 212. (The components introducing illumination light to microscope 250 have been omitted for clarity.) Fringes reflected from photomask 212 pass beam-combiner 210 and are partially reflected from beam-combiner 220. The image of phase probes 206 comes to a sharp focus in a plane 260 which is equidistant from beam-combiner 220 and camera 240; if an additional camera were to be inserted at this point, one would see an image of two small de-magnified apertures. At this point, however, the electric fields of phase components 205 are separate and distinct and not overlapped, so no fringes are visible in plane 260. Wavefront overlap is necessary for the production of fringes, and may be effected by placing non-imaging photodetector 231, placed just abaft aperture screen 230, at a position slightly displaced from the best-focus image plane 260. This action may be performed independently of photomask focus and without photomask probe image degradation. The required detector translation from plane 260 is on order of the depth-of-field of objective lens 211, and is typically several hundred nm at 193 nm wavelengths.

The purpose of the interferometric beam-processing module 102, 202 is to create two (or more) spatially and temporally coherent beam components 105, 205, the relative phase of which may easily be varied. This can be accomplished using either a Mach-Zehnder-type interferometer or by use of an opaque screen with multiple pinhole apertures in conjunction with the spatially coherent light source 101, 201.

Figure 3:
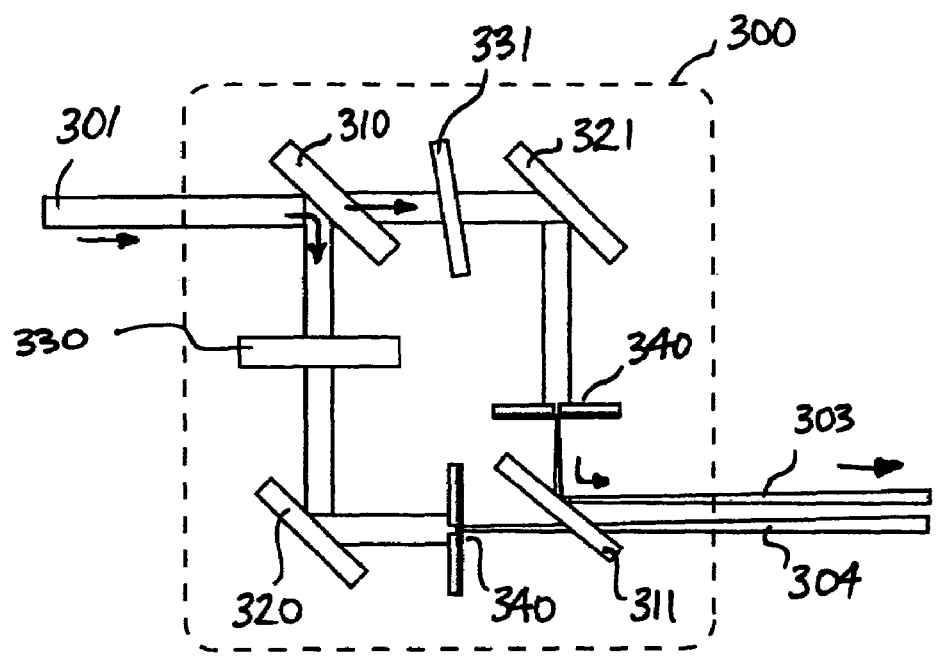
FIG. 3 A schematic diagram of a first embodiment of a Mach-Zehnder-type interferometric beam processing module.
Figure 6:
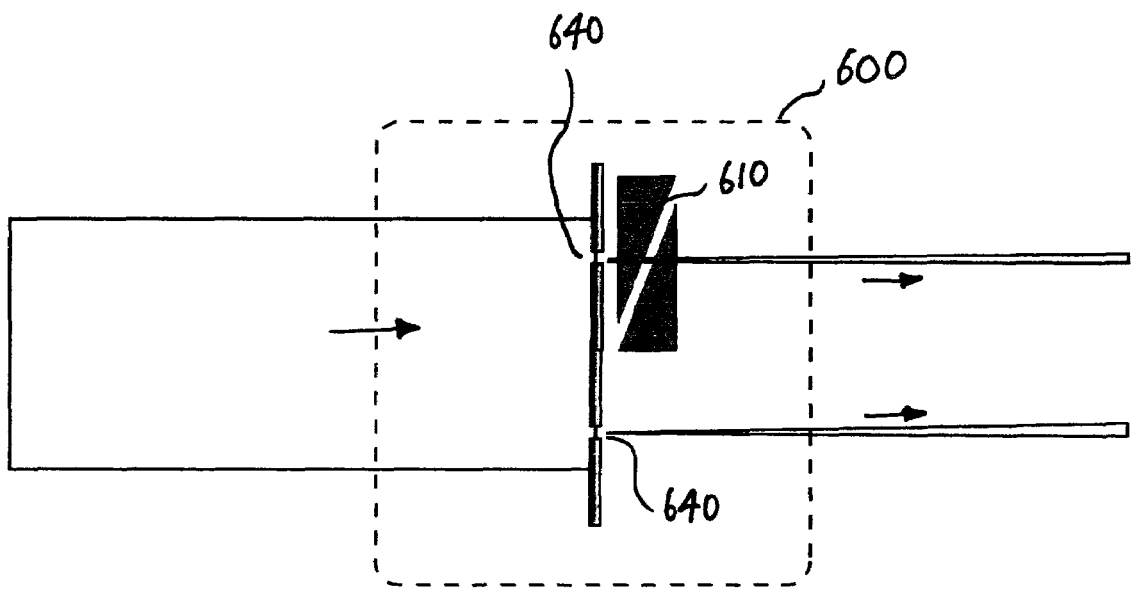
FIG. 6 A schematic diagram of a second embodiment of a dual-aperture-type interferometric beam processing module

A first embodiment for module 102, 202 is similar to a two-arm Mach-Zehnder (MZ) interferometer, and is shown schematically in FIG. 3. Interferometer 300 consists of two high-reflector (HR) mirrors 320, 321 and two beam-combiners 310, 311. Incident coherent light 301 is roughly equally divided by beam-combiner 310 to either arm of the interferometer. Each arm of interferometer 300 contains an aperture 340 mounted equidistantly from final beam combiner 311; both apertures are ultimately imaged with high de-magnification near the surface of photomasks 112, 212. One arm of interferometer 300 contains an optically thick element 331, by which the relative optical phase between beam components 303, 304 may be varied in a controlled fashion. Element 331 may be a rotating transparent window (which produces a quadratic phase shift with increasing plate angle), but preferably is a double-wedge optic, which produces a linear phase shift without beam-steerage. (A sliding optical wedge is shown in FIG. 6 as 610) The relative orientation and separation of the apertures 340 may be independently varied by means of adjustable mounts (not shown). Note that, unlike most MZ interferometers, beam components 303, 304 are not combined at the final beam-combiner 311 of interferometer 300, but remain separate (the separation is shown greatly exaggerated in FIG. 3) and are not overlapped until after they have sampled the photomask feature.

Figure 4:
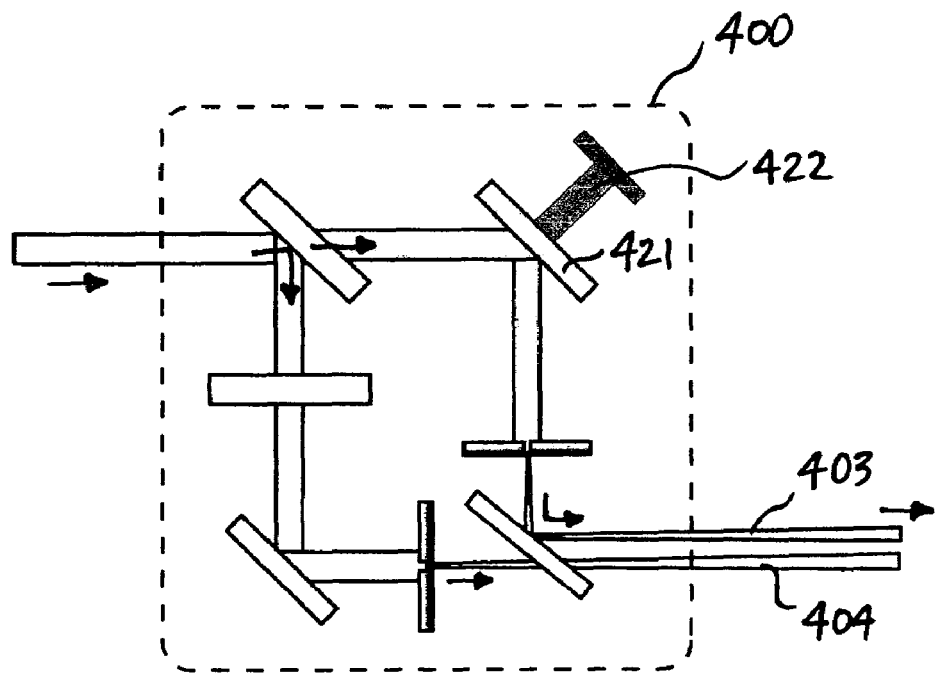
FIG. 4 A schematic diagram of a second embodiment of a Mach-Zehnder-type interferometric beam processing module.

A second embodiment for module 102, 202 is modified MZ interferometer 400, shown schematically in FIG. 4. In interferometer 400, the phase difference between the two beam components 403, 404 is adjusted by changing the physical length of one of the arms of interferometer 400. To this end, the optical element 331 has been removed in favor of mounting one of the HR mirrors 421 on a linear-motion 'push-pull' mount 422, e.g., a piezo-electric transducer or linear translation stage. Since only one or two waves of optical path difference between components 403, 404 is necessary during the course of the photomask measurement, the movable optic 421 needs only move several hundred nanometers at UV wavelengths.

Figure 5:
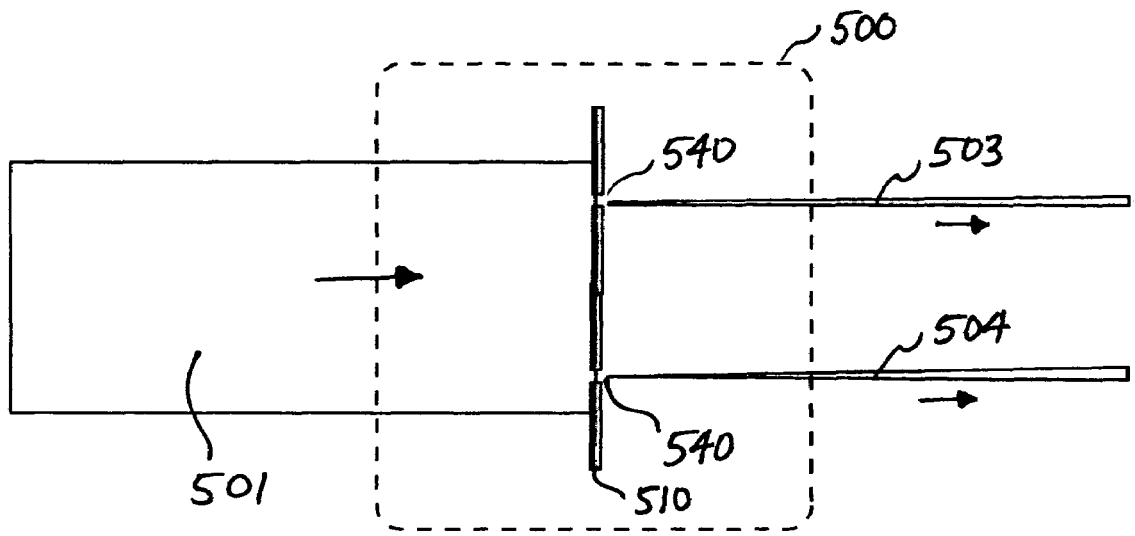
FIG. 5 A schematic diagram of a first embodiment of a dual-aperture-type interferometric beam processing module.

A different type of module 102, 202 is also possible. Two (or more) phase-coherent optical components may be generated by impinging a spatially-coherent wavefront onto a screen with a multitude of apertures, much like in the original Young's experiment. A first embodiment of a dual-aperture screen 500 that may be used as module 102, 202 is shown in FIG. 5. Screen 500 consists of two transparent apertures 540 located within opaque screen 510, and is placed in front of a coherent beam 501. Screens 500, 600 are oriented at an angle relative to the direction of propagation such that the longitudinal separation between apertures 540, 640 is less than the temporal coherence length of the illuminating light 501. This condition ensures high visibility fringes. Preferably, screens 500, 600 are perpendicular to beam 501. The spacing between apertures 540 is exaggerated for clarity. Compared to MZ interferometer modules 300, 400, this approach is simpler to implement and align, but it is somewhat more difficult to effect a phase or amplitude change between phase components 503, 504 due to their close proximity. Changes in phase may, for example, be introduced between the two apertures by inserting a transparent optic with a quadratic phasefront (i.e., a lens) either in front or in back of the aperture screen. Additionally, a specialized double-wedge optic 610 may be constructed which covers one or the other of apertures 640, as shown in FIG. 6.

To effect changes in aperture size, spacing, or orientation, a rotating wheel, upon which are mounted a number of screens of varying construction, may be implemented in either embodiment 500, 600.

With either embodiment of module 300, 400, 500, 600, the procedure for photomask phase measurement is the same. The tool operator simultaneously views both the (large area) microscope image of the photomask and the image of the phase probes in sharp focus, so that phase probes 106, 206 on photomask 112, 212 may be adjusted to suit the desired feature geometry. Typically, one phase probe is placed (by a combined motion of aperture 340, etc., and photomask 112, 212 using adjustable stage 113, 213) over the unknown feature, and the other phase probe over a bare quartz substrate ("clear") area.

The phase-coherent probes 106, 206 form stationary non-localized fringes above and beneath the photomask. As discussed previously, this duality allows for two phase measurement modes: transmission and reflection. In transmission mode, the beams that transit the photomask are collected by condenser lens 120 and are sampled by either a fixed-position point detector (photosensitive detector 131 situated behind an aperture 130), or in their entirety, by an appropriate camera 141. Generally, the size of phase probes 106, 206 are beneath the spatial resolution of condenser lens 120; therefore, the condenser lens cannot resolve the two separate probes. In these cases, the probe wavefronts overlap completely, and the fringe structure covers the entire image field of condenser lens 120. Larger probes will experience less overlap. Transmission mode is ideally suited for EAPSMs. Since embedded-attenuators exhibit only approximately 5–10% transmission, the transmitted wavefronts are of different intensity, which may affect the fringe visibility. To help balance the signal levels and restore fringe visibility, variable attenuator 330 may be placed in one arm of MZ interferometer 300, 400.

One method to determine the phase shift of a photomask feature, in either transmission or reflection mode, is point-by-point sampling of the fringe structure. For each value of phase delay between phase probes 106, 206, detectors 131, 231 record a light value which depends upon the position and visibility of the fringe. Changing the phase delay between phase probes 106, 206 causes the interference fringe positions to shift relative to fixed-position detector 131, 231 located above or beneath the photomask, and a (typically) sinusoidal intensity curve may be recorded. Multiple light pulses may be averaged by the detection electronics for each increment in the phase delay to reduce measurement error. The phase plots from the unknown feature site and the clear site are then compared and the OPD of the unknown feature may be determined graphically or through curve-fitting. It is advantageous to employ the techniques of phase-shifting interferometry (PSI) to reduce required data sets and measurement times.

The OPD of the photomask feature may also be determined by sampling the entire fringe pattern simultaneously, rather than in a point-by-point fashion. This may be accomplished in either reflection or transmission mode through use, e.g., of camera 141. Software algorithms can then be employed to curve-fit the fringe structure from the camera image. The phase shift of the unknown feature is then determined from the shift in the fringe structure when the position of phase probes 106, 206 is adjusted on the photomask surface.

From this basic description, a number of different methods and architectures may immediately be envisioned and applied by those skilled in the art to the determination of the phase shift of a given photomask feature. The interferometric/beam processing module may be of several different forms, the fringes may be measured above or below the photomask, and these fringes may be captured point-by-point or in their entirety. Each version of the processing module may be combined with any of the measurement techniques to determine the phase of photomask features at extremely high spatial resolutions. Further refinements are possible, for example, optical polarization can be harnessed to create multiple sets of independent, non-interfering phase probes for additional measurement flexibility. Accordingly, the scope of the invention should be determined by the following claims and their legal equivalents.

What is claimed is:

1. An architecture for the measurement of photomask optical path difference, comprising:

A spatially coherent light source;

An interferometric beam processing module;

An optical microscope; and

A photosensitive detector;

Wherein said module is disposed to receive and divide light from said light source into a number of phase-coherent light beams, each of which passes through an aperture;

Wherein said microscope is disposed to image the multitude of said apertures in said module with a given demagnification onto a photomask in order to create a multitude of phase probes; and Wherein said detector is disposed to receive the transmitted fringe pattern caused by the interference of the multitude of said phase probes.

2. The architecture of claim 1 wherein said light source is a laser with a wavelength that is approximately the same as the actinic wavelength of said photomask.

3. The architecture of claim 1 wherein said optical demagnification of said apertures is greater than 50.

4. The architecture of claim 1 wherein said module is of the Mach-Zehnder (MZ) interferometer type.

5. The architecture of claim 1 wherein the relative optical phase between said phase probes may be varied by suitable adjustments to said module.

6. The architecture of claim 1 wherein said module is a dual-aperture screen.

7. The architecture of claim 1 wherein said detector is a UV-sensitive CCD camera.

8. The architecture of claim 1 wherein said detector is a photomultiplier tube (PMT).

9. The architecture of claim 1 wherein the number of said phase probes is two (2).

10. The apparatus of claim 1 wherein said module is of the Twyman-Green interferometer type.

11. An architecture for the measurement of photomask optical path difference, comprising:
   A spatially coherent light source;
   An interferometric beam processing module;
   An optical microscope; and
   A photosensitive detector;
   Wherein said module is disposed to receive and divide light from said light source into a number of phase-coherent light beams, each of which passes through an aperture;
   Wherein said microscope is disposed to image the multitude of said apertures in said module with a given demagnification onto a photomask in order to create a multitude of phase probes; and
   Wherein said detector is disposed to receive the reflected fringe pattern caused by the interference of the multitude of said phase probes.

12. The architecture of claim 11 wherein said light source is a laser with a wavelength that is approximately the same as the actinic wavelength of said photomask.

13. The architecture of claim 11 wherein said optical demagnification of said apertures is greater than 50.

14. The architecture of claim 11 wherein said module is of the Mach-Zehnder (MZ) interferometer type.

15. The architecture of claim 11 wherein the relative optical phase between said phase probes may be varied by suitable adjustments to said module.

16. The architecture of claim 11 wherein said module is a dual-aperture screen.

17. The architecture of claim 11 wherein said detector is a UV-sensitive CCD camera.

18. The architecture of claim 11 wherein said detector is a photomultiplier tube (PMT).

19. The architecture of claim 11 wherein the number of said phase probes is two (2).

20. The apparatus of claim 1 wherein said module is of the Twyman-Green interferometer type.

* * * * *